(12) United States Patent
Krishnamurthy (10) Patent No.: US 6,399,314 B1
(45) Date of Patent: Jun. 4, 2002

(54) METHODS OF DETECTION OF AMYLOIDOGENIC PROTEINS

(75) Inventor: Girija Krishnamurthy, Chestnut Ridge, NY (US)

(73) Assignee: American Cyanamid Company, Madison, NY (US)

( * ) Notice: Subject to any disclaimer, the term of this patent is extended or adjusted under 35 U.S.C. 154(b) by 0 days.

(21) Appl. No.: 09/474,970

(22) Filed: Dec. 29, 1999

(51) Int. Cl.$^7$ .................. G01N 33/53; A01N 61/00; A61K 31/00; C07K 16/00
(52) U.S. Cl. .................. 435/7.1; 514/1; 514/2; 530/387.1
(58) Field of Search .................. 514/1, 2; 435/7.1; 530/387.1

(56) References Cited

U.S. PATENT DOCUMENTS 5,276,059 A    1/1994   Caughey et al. ............ 530/387

FOREIGN PATENT DOCUMENTS

| WO | WO 94/01116 | 1/1994 | ......... A61K/31/655 |
| WO | WO 97/07402 | 2/1997 | ......... G01N/33/68 |
| WO | WO 99/08695 | 2/1999 | ......... A61K/38/00 |

OTHER PUBLICATIONS

Irvine et al. Biochemical Society Transactions (1998), vol. 26(1) p. S36.*
Pollack et al., Neurosci. Lett., 1995, 197:211–214.
Tjernberg et al., Chemistry & Biology, 1999, 6:53–62.
Woody, R.W., "The Circular Dichroism of Biopolymers", Proc. F.E.C.S. Int. Conf. Circ. Dichroism, 1987 (meeting date 1985), pp. 270–295.
Lorenzo et al., 1994, Nature 368:758–760.
Lorenzo et al., 1994, Proc. Natl. Acad. Sci. USA, 91 (25):12243–12247.
Burgevin et al., NeuroReport, 1994, 5:2429–2432.
Fraser et al., Biophys. J., 1991, 60 (5):1190–1201.
Szmacinski et al., Biophys. Chem., 1996, 62:109–120.
LeVine Protein Science, 1993, 2:404–410.
Burdick et al. J. Biol. Chem. 1992, 267:546–554.
LeVine, J. Exp. Clin. Invest., 1995, 2:1–6.
Pollack et al., Neuroscience Letters, 197, 1995, 197:211–214.
Lorenzo et al., Proc. Natl. Acad. Sci. USA, 91, 1994, (25):12243–12247.
Fraser et al., Biophys. J., 1991, 60 (5):1190–1201.
Klunk, W.E. et al. "Two simple Methods for Quantifying Low–Affinity Dye–Substrate Binding" Journal of Histochemistry and Cytochemistry, 1989, vol. 37, No. 8, pp. 1293–1298, U.S.A., ISSN:0022–1554.
Guijarro J. Inaki, et al. "Amyloid Fibril Formation by an SH3 Domain" Proceedings of the National Academy of Sciences of the United States, Apr. 14, 1998, vol. 95, No. 8, pp. 4224–4228, U.S.A., ISSN: 0027–8424.

* cited by examiner

Primary Examiner—Jezia Riley
(74) Attorney, Agent, or Firm—Darby & Darby (57) ABSTRACT

A method/assay for detecting various aggregated forms of amyloid peptide using amyloid-specific spectroscopic probes, such as Congo red and related analogs, is described. Such an assay could be used to assess the aggregation state of the peptide in the presence of other potential inhibitors of fibrillogenesis, providing a useful model by which to test inhibitors of aggregation in in vitro models. Results of such an assay can be useful in determining the stage at which the process of aggregation can be intervened to reduce the toxicity of amyloid peptide to neuronal cells. In specific examples, circular dichroism, UV absorption, and fluorescence spectroscopy are each used to evaluate the aggregation form of β-amyloid peptide.

27 Claims, 4 Drawing Sheets

METHODS OF DETECTION OF AMYLOIDOGENIC PROTEINS

FIELD OF THE INVENTION

The present invention relates to methods for evaluating aggregated forms of amyloid polypeptides. The invention further relates to methods for testing potential inhibitors of amyloidosis in vitro or in vivo in order to develop new therapies for diseases or disorders associated with amyloidosis, such as Alzheimer's disease.

BACKGROUND OF THE INVENTION

Alzheimer's disease is characterized by the presence of cerebral amyloid plaques deposited around nerve cells, which eventually erode and destroy the normal processes of the brain. The primary protein component of such plaques is the aggregated form of the 39 to 43 residue isoforms of the β-amyloid protein (Aβ). The primary pathogenic event in Alzheimer's disease is the formation of these fibrillar amyloid plaques in the brain parenchyma and vasculature. Deposition of fibrillar aggregates of these amyloid polypeptides has been shown to be due to the self assembly of the polypeptides into macromolecular structures consisting of a cross-β-sheet conformation, which is toxic to cultured neuronal cells.

A goal of treating Alzheimer's disease is to prevent aggregate formation and/or to therapeutically administer an inhibitor of aggregate formation after the disease has been diagnosed, in order to reverse the toxic effects of the protein. Agents that block the formation of macromolecular aggregates can thus potentially act to inhibit cytotoxicity and are of pharmaceutical interest because they can potentially act as anti-Alzheimer's drugs. Among the several small molecules reported to be aggregation inhibitors, Congo red, a biphenyl diazo sulphonated dye, is reported to be a neuroprotective compound (Pollack et al., Neurosci. Lett., 1995, 197:211–214; Lorenzo et al, Proc. Natl. Acad. Sci. USA, 1994, 91:12243–12247; and Burgevin et al., NeuroReport, 1994, 5:2429–2432).

PCT Application PCT/US93/06637 (the "'637 application") describes the use of Congo red and its pharmaceutically acceptable salts, or derivatives thereof, for treating amyloidogenic diseases, among them Alzheimer's disease. Congo red reportedly interferes with amyloidosis or destabilizes already formed amyloid structures. These properties establish a basis for the '637 application to advocate administration of Congo red for treatment of conditions associated with the deposition of amyloidogenic protein in plaques. Congo red, as a therapeutic agent, may be administered in vivo in sufficient quantity to interfere with amyloidogenic protein formation or the destabilization of amyloid already formed. Thus, Congo red reportedly not only binds amyloid plaques, but can also inhibit the accumulation of amyloidogenic protein.

Congo red's value and effectiveness as a possible treatment for Alzheimer's disease require further examination because Congo red cannot cross the blood brain barrier. Derivatives, analogues, salts, etc. of Congo red may have the same mode of action on β-amyloid peptides as Congo red, i.e., such derivatives may also be neuro-protective.

Currently, antibody-based methods and fluorescence methods using Thioflavin T are being used to detect aggregated peptide for screening anti-Alzheimer's agents. A fluorescence correlation spectroscopy method has been used to determine polymerization of amyloid peptide (Tjernberg et al., Chemistry & Biology, 1999, 6:53–62). However, these techniques do not differentiate various conformational forms of aggregated polypeptide.

An assay for detecting alternate conformational forms of aggregated amyloid polypeptide is not disclosed in the prior art. Such assays optimally can be used to rapidly assess the aggregation state of the polypeptide, especially in the presence of inhibitors of fibrillogenesis.

Thus, there is a need in the art for methods for probing amyloidosis and amyloid plaques, which in turn addresses the need to study the process by which amyloidogenic proteins cause Alzheimer's disease. Specifically, there is a need to develop assays involving biophysical and analytical methods to characterize the conformation and aggregation state of aggregates of amyloid polypeptide and to discriminate the effect of potential inhibitors of amyloidosis, specifically in Alzheimer's disease. Since very little is known about the nature of toxic aggregates in Alzheimer's disease and the mechanism of formation of these aggregates in the brain, a combination of assays are necessary to determine if potential inhibitors are producing the desired effect in in vitro test systems. Assays are also needed to determine the effect of test compounds on conformation of amyloid polypeptide in bodily fluids such as plasma or cerebral spinal fluid.

SUMMARY OF THE INVENTION

This invention provides methods to detect various aggregated forms of amyloid polypeptide, for example, using amyloid-specific dyes, such as Congo red and other related analogs, or fluorophore-labeled amyloid peptides. The methods are useful in determining the aggregated state of the polypeptide as well as to test modulators of aggregation in in vitro models. The method can be used in determining the stage at which intervention in the process of aggregation reduces toxicity, e.g., Aβ peptide to neuronal cells. The methods can also be used to determine the effects of inhibitor or anti-Alzheimer's agent for therapeutic or prophylactic treatment of amyloidosis or other related diseases.

Thus, in one aspect, the present invention provides a method for determining an aggregation conformation of an amyloid polypeptide. This method comprises correlating a spectroscopic property of a complex of an amyloid-specific spectroscopic probe, such as a sulphonated diazo dye or fluorophore-labeled amyloid peptide contacted with the amyloid polypeptide under conditions that permit aggregation of the polypeptide, with a predetermined spectroscopic property of a complex of the amyloid-specific probe with aggregated amyloid polypeptide of known conformation.

In a further aspect, the invention provides a method for detecting an effect of a test compound for inhibition, disruption, or disaggregation of amyloid formation. This method comprises correlating spectroscopic properties of (a) a complex of an amyloid-specific spectroscopic probe, such as a sulphonated diazo dye or a fluorophore-labeled amyloid peptide, contacted with an amyloid polypeptide and a test compound under conditions that permit aggregation of the polypeptide, and (b) a complex of the amyloid-specific spectroscopic probe contacted with the amyloid polypeptide under conditions that permit aggregation (control). The spectroscopic probe can be contacted with the sample prior to aggregation or, if it is an amyloid-specific dye, after aggregation. If the spectroscopic probe is a fluorophore-labeled peptide, it should be permitted to aggregate with the amyloid polypeptide. The test compound can be added prior to or after aggregation. A difference in the spectroscopic properties indicates that the test compound has an effect on amyloid formation.

DETAILED DESCRIPTION OF THE INVENTION

The present invention describes assays that can be used to detect conformation differences in various aggregated forms of amyloid polypeptide. The invention is based, in part, on observations of the effect of Congo red, a fluorescent amyloid-specific spectroscopic probe, on aggregation. The effects were determined by adding the Congo red to the amyloid polypeptide (Aβ peptide) solution at the start of aggregation in one experiment, and to preformed aggregates in another experiment. Congo red was found to form at least two distinct complexes with β-amyloid in vitro. Congo red combined with the Aβ-peptide prior to the aggregation of the peptide into β-sheets had different spectral properties than when combined with the Aβ peptide after it was already aggregated into β-sheets (the so-called fibrillar peptide). Congo red acted to prevent the formation of fibrillar aggregates of the Aβ peptide, and also reduced the toxic effects of the already aggregated peptide. Although the resulting complexes of coaggregates and Congo red complexes with fibrillar forms were shown to be different by spectroscopic analysis, in both instances, the toxic effects of the peptide were reduced by the addition of Congo red.

Experimental results indicate that the molecular mechanisms leading to the reduction in toxicity are significantly different in the two instances. Application of these results facilitates determination of the stage at which intervention in the aggregation process optimally reduces the toxicity, e.g., to nerve cells. The methods can also be used to identify the various protein complexes that result from different polypeptides combining with a prototype small inhibitor molecule. Assays which can be used to rapidly assess the aggregation state of the amyloid polypeptide in the presence of potential inhibitors of fibrillogenesis are described.

Aβ-peptide is known to mediate toxicity and is believed to be involved in neuronal cell death in Alzheimer's disease. Currently there is tremendous interest in identifying proteins that mediate neurotoxicity of Aβ-peptide. The methods described here can be used to characterize the interactions of Aβ-peptide in its aggregated form(s) with the proteins and to also determine if potential test compounds disrupt the interactions. The application of the methods also provides additional insights into the molecular mechanisms of Alzheimer's disease, which is currently the basis of drug discovery efforts in neurodegeneration. These discoveries can be applied to evaluate other amyloid polypeptides as well.

Three different techniques were implemented as tools to determine the extent of aggregation of the polypeptide, in the presence and absence of Congo red. The effect inhibitors have on the self assembly of amyloid polypeptide and the coincidental effect on cytotoxicity was also examined.

1. Circular dichroism (CD) spectroscopy was implemented to identify and differentiate the conformations of the amyloid polypeptide that was aged in the presence or absence of Congo red. The method is based upon changes in CD absorption of amyloid polypeptide in the far UV and Congo red in the near-UV region. Both the far-UV and the near-UV spectra of the aggregate-complexes were scanned. Far-UV CD spectra were useful in determining the secondary structure of the amyloid polypeptide. Near-UV CD spectra were useful for differentiating Congo red complexes. Amyloid polypeptide alone in buffer and free Congo red did not produce an appreciable CD absorption signal in the near-UV region. Since Congo red does not have an intrinsic CD spectrum in the free state, spectral changes induced upon binding to the amyloid proteins are useful in identifying various forms of amyloidogenic proteins. The induced CD absorption effects are distinctly different for coaggregates of Congo red with amyloid polypeptide and complexes of Congo red with preformed-aggregates or fibrillar form of polypeptide. While not intending to be bound by any particular theory, the changes in the near-UV CD spectrum of Congo red are believed to be due to induction of a chiral environment upon binding to ordered fibrillar form of the protein.

The near-UV CD spectrum of coaggregates (of amyloid polypeptide and Congo red) was shown to be significantly different than that of the preformed fibrillar complexes contacted with Congo red. The observed differences in the spectra of the complexes was due to the formation of different complexation states of Congo red. The exciton coupled CD spectra of preformed fibrils was indicative of complexation of Congo red with an ordered β-sheet conformation of peptide (i.e., due to the formation of twisted β-sheet structures; Woody, R. W., "The Circular Dichroism of Biopolymers", Proc. F.E.C.S. Int. Conf. Circ. Dichroism, 1987 (meeting date 1985), pp. 270–295), while the spectrum of the coaggregates was consistent with complexation of Congo red with intermediate aggregated structures.

The CD spectrum of aggregated amyloid polypeptide was scanned at various time points to correlate the formation of thioflavin-binding macromolecular assemblies (aggregates) with the appearance of β-sheet conformation. Fluorescence spectroscopy using Thioflavin (ThT) binding was used to confirm β-sheet formation in the polypeptide. The induced fluorescence due to thioflavin is specific for amyloid β-pleated fibrils, but not for other β-sheet structures or for the soluble oligomeric forms of the polypeptide.

2. UV spectroscopy was used to differentiate the Congo red absorption spectra of the two complexes of preformed fibrils and coaggregates. The changes in the absorption spectra of Congo red in the presence and absence of amyloid polypeptide is determined, as are the changes in the environment of Congo red upon binding to fibrillar, non-fibrillar, and other alternate forms of complexes.

3. Fluorescence spectroscopy was used to differentiate complexes of Congo red. Congo red binds to preformed fibrils as well as to intermediate aggregate forms of the amyloid polypeptide. The intrinsic fluorescence of Congo red is significantly enhanced when it is bound to the aggregated form. The fluorescence excitation spectrum of Congo red in the aggregate-bound state is also red shifted relative to the free form of the polypeptide. Changes in the fluorescence properties of Congo red are dependent on the aggregated state of the Congo red. The differences in the observed spectral characteristics of the coaggregates and complexes of the fibrillar polypeptide with Congo red are due to the differences in the relative hydrophobicity of the binding sites and to the number of bound Congo red molecules in the complexes with preformed fibrils and coaggregates.

In the present invention, Congo red has been shown to promote the formation of a stable intermediate in a $\beta$-sheet conformation when coaggregated with amyloid polypeptide. Although Congo red binds preformed fibrils as well as intermediate aggregate forms of amyloid polypeptide, there was no evidence of interaction with the polypeptide in random coil state. Results show that the fluorescence spectrum of Congo red when co-aggregated with the amyloid polypeptide is enhanced eight-fold relative to the free form. Preformed fibrils have also been shown to bind Congo red, but the fluorescence enhancement of the complex between preformed fibrils and Congo red is only enhanced two-fold relative to the free form of Congo red. Thus, using fluorescent techniques, the present study shows that Congo red has a dual mode of interaction with $\beta$-amyloid protein 1–40. Since $A\beta_{39-43}$ isoforms also convert from random coil to $\beta$-sheet form, interactions of Congo red should be similar for all isoforms of $A\beta$ peptide.

The spectroscopic results described in this invention have shown that inhibitors such as Congo red form at least two distinct complexes with amyloid polypeptides. Both the preformed fibrils and coaggregates have been shown to form large molecular weight substances when bound to Congo red (approximately 50 kD or greater). Although Congo red binds to the intermediate aggregates of $A\beta$ peptide, and therefore attenuates the toxicity of the fibrillar peptide, formation of "insoluble" complexes in the coaggregates can still occur, suggesting that test compounds that produce such effects on aggregation need to be investigated in terms of their suitability for therapeutic or prophylactic action in Alzheimer's disease.

Based on these specific observations, which are described in greater detail in the Examples, infra, the general ability of a fluorescent probe, i.e., a sulphonated diazo dye or a fluorophore-labeled amyloid peptide, to probe the aggregation form of aggregated amyloid polypeptide has been discovered. This analytical tool provides a basis for various screening techniques for the ability of test compounds to inhibit or reverse amyloidosis.

Various embodiments and aspects of the invention are discussed herein. The specific headings (bold, underlined) and sub-headings (bold, italic, underlined) are provided to facilitate understanding of the invention, and are not intended to be limiting.

General Definitions

The terms "amyloid," "amyloid plaque," and "amyloid fibril" refer generally to insoluble proteinaceous substances with particular physical characteristics independent of the composition of proteins or other molecules that are found in the substance. Amyloid can be identified by its amorphous structure, eosinophilic staining, changes in thioflavin fluorescence, and homogeneous appearance. Protein or peptide components of amyloid are termed herein "amyloid polypeptides," and include, but are not limited to, $\beta$-amyloid peptide ($A\beta$), including synthetic $\beta APs$ corresponding to the first 28, 40, or 42 amino acids of $A\beta$, i.e., $A\beta(1-28)$, $A\beta(1-40)$, $A\beta(1-42)$, respectively, as well as a synthetic $\beta AP$ corresponding to amino acids 25–35 of $A\beta$, i.e., $A\beta_{25-35}$; scrapie protein precursor or prion protein; immunoglobulin, including $\kappa$ or $\lambda$ light or heavy chains, or fragments thereof, produced by myelomas; serum amyloid A; $\beta_2$-microglobulin; apoA1; gelsolin; cystatin C; (pro) calcitonin; atrial natururetic factor; islet amyloid polypeptide, also known as amylin (see, Westermark et al., Proc. Natl. Acad. Sci. USA, 1987, 84:3881–85; Westermark et al., Am. J. Physiol., 1987, 127:414–417; Cooper et al., Proc. Natl. Acad. Sci. USA, 1987, 84:8628–32; Cooper et al., Proc. Natl. Acad. Sci. USA, 1988, 85:7763–66; Amiel, Lancet, 1993, 341:1249–50); and the like. For purposes of this disclosure, amyloid polypeptide can aggregate spontaneously by induction, e.g., with a seed, under conditions that permit aggregation. It should be noted that although human amylin aggregates spontaneously in vitro, rat amylin, which differs from human amylin at six amino acid residues, is non-amyloidogenic and does not form fibrils (see, Lorenzo et al., Nature, 1994, 368:756–760). In a specific aspect, the term "amyloid" is used herein to refer to substances that contain $A\beta$. "Amyloidosis" refers to the in vivo deposition or aggregation of proteins to form amyloid plaques or fibrils.

The term "amyloid-specific spectroscopic probe" refers to an amyloid binding dye compound or peptide-fluorophore conjugate that interacts with aggregated forms of amyloid, and demonstrates different spectroscopic properties depending on the conformation of the aggregate. Naturally, as one of ordinary skill in the art can readily appreciate, a fluorophore will necessarily act as a chromophore, i.e., it will have a specific absorption spectrum. Moreover, when constrained in aggregated amyloid, it will likely have an induced CD spectrum. The probe may, and preferably will, affect amyloidogenesis. Sulphonated diazo dyes and fluorophore-labeled amyloid peptides are both examples of amyloid-specific spectroscopic probes.

A "fluorophore-labeled amyloid peptide" is an amyloid polypeptide-derived peptide, such as $A\beta$, conjugated with a fluorophore (fluorescent molecule). Amyloid peptides can be amyloid polypeptides, or portions thereof capable of co-aggregating with amyloid polypeptides. Fluorophore-labeled amyloid peptides, however, need not be capable of aggregation on their own. Examples of fluorphores for labelling the amyloid peptide include but are not limited to fluorescein, Texas red, ruthenium $\beta$-pyridyl complexes, and rhodamine. Fluorophore also have useful absorption spectra in the UV, and may also have useful IR spectra properties. Preferably, the fluorophore-labeled amyloid peptide represents about 10% or less, more preferably about 1% or less, and most preferably about 0.1% or less of total peptide in the sample.

In its broadest sense, "an amyloid-binding" dye is a chromophore that has a propensity to associate with amyloid. Preferably, the dye is also a fluorophore, i.e., capable of fluorescence, under specific conditions. For purposes of the present invention, and in the study of amyloidosis, the paradigmatic dye is a sulphonated diazo dye, and more particularly Congo red (see, e.g., U.S. Pat. No. 5,276,059 and PCT/US93/06637). However, related compounds or equivalents of Congo red, such as chrysamine G, which is a carboxylate analog of Congo red, are contemplated as within the scope of the invention. The structure of Congo red and chrysamine G are shown below:

Congo Red

Chrysamine G

Conditions that permit aggregation are pH, ionic strength, temperature and low, preferably no, or at least no detectable, concentrations of any chaotropic or lyotropic reagents, such that an amyloid polypeptide can aggregate. The presence of an amyloid "seed" increases the propensity of polypeptide to aggregate.

An "aggregation complex" refers to the complex formed by interaction of an amyloid-specific spectroscopic probe, such as Congo red, with aggregated amyloid polypeptide. This complex can form as a result of co-aggregation, i.e., where the amyloid-specific spectroscopic probe is present with the amyloid polypeptide prior to induction of aggregation. Alternatively, the complex can form as a result of interaction of the dye with a pre-formed amyloid polypeptide aggregate.

The term "aggregation form" is used herein to refer to the structure or conformation adopted by the amyoid polypeptide in its aggregated state. For example, aggregated Aβ can form a β-sheet or a twisted β-sheet form. As a practical matter, the secondary and quaternary (peptide-peptide) conformation is represented by differences in spectroscopic properties. In other words, without knowing precisely the structure of the aggregated amyloid polypeptide, by detecting differences in spectroscopic properties of either the polypeptide or the amyloid-specific spectroscopic probe, one can detect structural differences. These differences in turn can be evaluated in vitro or in vivo for their effect on cellular toxicity or amyloidosis-associated pathogenicity.

The term "polypeptide aggregate" or "aggregate" refers to self-associated species of polypeptide that form either fibrillar or non-fibrillar forms and to those that are toxic or non-toxic to neuronal cultures.

As used herein, the term "spectroscopic property" refers to the amount of radiation absorbed by the aggregated complex, or energy radiated from the aggregated complex excited by absorption of radiation. In a specific embodiment, circular dichroism (CD) ultraviolet (UV) spectra are obtained in the far-UV and near-UV ranges. In another embodiment, UV absorption spectra are obtained. In yet a further embodiment, fluorescence emission spectra are obtained. In still a further embodiment, infrared (IR) spectra are obtained. Generally, spectra are obtained by measuring the difference between the amount of light transmitted or absorbed at a given wavelength in a sample containing the aggregated complex versus a reference sample. Fluorescence spectra are obtained by detecting the strength of emission at a given excitation light wavelength. Fluorescence excitation spectra can be obtained by evaluating the strength of fluorescence as a function of absorption wavelength. These concepts are well known in the art (see, e.g., Cantor and Schimmel, *Biophysical Chemistry*, W. H. Freeman and Company: San Francisco, 1980; Silverstein et al., *Spectrometric Identification of Organic Compounds*, John Wiley & Sons: New York, 1981).

A disease or disorder is associated with amyloidosis when amyloid deposits or amyloid plaques are found in or in proximity to tissues affected by the disease, or when the disease is characterized by overproduction of a protein that is or can become insoluble. The amyloid plaques may provoke pathological effects directly or indirectly by known or unknown mechanisms. Examples of amyloid diseases include, but are not limited to, systemic diseases, such as chronic inflammatory illnesses, multiple myeloma, macroglobulinemia, familial amyloid polyneuropathy (Portuguese) and cardiomyopathy (Danish), systemic senile amyloidosis, familial amyloid polynephropathy (Iowa), familial amyloidosis (Finnish), Gerstmann-Straussler-Scheinker syndrome, familial amyloid nephropathy with urticaria and deafness (Muckle-Wells syndrome), medullary carcinoma of thyroid, isolated atrial amyloid, and hemodialysis-associated amyloidosis (HAA); and neurodegenerative diseases.

Type II diabetes is associated with amyloid fibrils or deposits of the pancreas, in particular the islet cells that produce insulin. As with the amyloid plaques of Alzheimer's disease, the amyloid plaques or fibrils of Type II diabetes provoke pathological effects. In particular, concentrations of human amylin at which fibrils form are toxic for human and rat pancreatic islet insulin-producing β-cells (Lorenzo et al., 1994, Nature 368:758–760). Accordingly, in a specific embodiment, the invention relates to Type II diabetic amyloidosis.

Chronic inflammatory illnesses, such as idiopathic familial Mediterranean fever, Muckle-Wells syndrome, chronic malarial infection, and the like, can result in expression of serum amyloid A, an acute phase protein which may undergo further processing and form amyloid deposits and plaques. For example, in the Third World, chronic malaria can lead to amyloidosis of the spleen and/or liver of an individual. The resulting organ failure can ultimately lead to death. Multiple myeloma is associated with overproduction of immunoglobulins, which immunoglobulins or fragments thereof can form amyloid deposits and plaques in organs or tissues in contact with the circulatory system. Deposition of transthyretin can result in familial amyloid polyneuropathy (Portuguese), familial amyloid cardiomyopathy (Danish), or systemic senile amyloidosis. Hemodialysis-associated amyloidosis is a complication among long-term hemodialysis patients, in which $\beta_2$-microglobulin is a major protein constituent of the amyloid fibrils (Drüeke, 1991, Miner. Electroyte Metab. 17:261–272; Geyjo et al., 1985, Biochem. Biophys. Res. Commun. 129:701–706; Gorevic et al., 1986, Proc. Natl. Acad. Sci. USA 83:7908–12; Shirahama et al., 1985, Lab. Invest. 53:705–709).

As noted above, in addition to systemic amyloidosis, the present invention relates particularly to neurodegenerative diseases involving amyloidosis. The term "neurodegenerative disease" refers to a disease or disorder of the nervous system, particularly involving the brain, that manifests with symptoms characteristic of brain or nerve dysfunction, e.g., short-term or long-term memory lapse or defects, dementia, cognition defects, balance and coordination problems, and emotional and behavioral deficiencies. Such diseases are "associated with amyloidosis" when histopathological (biopsy) samples of brain tissue from subjects who demonstrate such symptoms would reveal amyloid plaque formation. As biopsy samples from brain, especially human brain, are obtained with great difficulty from living subjects or might not be available at all, often the association of a symptom or symptoms of neurodegenerative disease with amyloidosis is based on criteria other than the presence of amyloid deposits, such as plaques or fibrils, in a biopsy sample.

In a specific embodiment, according to the present invention the neurodegenerative disease associated with amyloidosis is Alzheimer's disease (AD). In other embodiments, the disease may be the rare Swedish disease characterized by a double KM to NL mutation in amyloid precursor protein (APP) near the amino-terminus of the βAP portion of APP (Levy et al., 1990, Science 248:1124–26). Another such disease is hereditary cerebral hemorrhage with amyloidosis (HCHA or HCHWA)-Dutch type (Rozemuller et al., 1993, Am. J. Pathol. 142:1449–57; Roos et al., 1991, Ann. N.Y. Acad. Sci. 640:155–60; Timmers et al., 1990, Neurosci. Lett. 118:223–6; Haan et al., 1990, Arch. Neurol. 47:965–7). Other such diseases known in the art and within the scope of the present invention include, but are not limited to, sporadic cerebral amyloid angiopathy, hereditary cerebral amyloid angiopathy, Down's syndrome, Parkinson-dementia of Guam, and age-related asymptomatic amyloid angiopathy (see, e.g., Haan and Roos, 1990, Clin. Neurol. Neurosurg. 92:305–310; Glenner and Murphy, 1989, N. Neurol. Sci. 94:1–28; Frangione, 1989, Ann. Med. 21:69–72; Haan et al., 1992, Clin. Neuro. Neurosurg. 94:317–8; Fraser et al., 1992, Biochem. 31:10716–23; Coria et al., 1988, Lab. Invest. 58:454–8). The actual amino acid composition and size of the βAP involved in each of these diseases may vary, as is known in the art (see above, and Wisniewski et al., 1991, Biochem. Biophys. Res. Commun. 179:1247–54 and 1991, Biochem. Biophys. Res. Commun. 180:1528 [published erratum]; Prelli et al., 1990, Biochem. Biophys. Res. Commun. 170:301–307; Levy et al., 1990, Science 248:1124–26).

In a further aspect, the neurodegenerative disease is a subacute spongiform encephalopathy, such as but not limited to, scrapie, Creutzfeldt-Jakob disease, Gerstmann-Sträussler disease, kuru, chronic wasting disease of mule-deer and elk, bovine spongiform encephalopathy of cattle, and mink transmissible encephalopathy.

The instant invention contemplates evaluating the aggregation form of an amyloidogenic polypeptide from any animal, and more preferably, mammal, including humans, as well as mammals such as dogs, cats, horses, cows, pigs, guinea pigs, mice and rats.

As used herein, the term "about" or "approximately" means within 50% of a given value, preferably within 20%, more preferably within 10%, more preferably still within 5%, and most preferably within 1% of a given value. Alternatively, the term "about" or "approximately" means that a value can fall within a scientifically acceptable error range for that type of value, which will depend on how qualitative a measurement can be given the available tools. "About" or "approximately" may define a distribution around a mean value, rather than a single value.

Induction of Amyloid Formation

In general, aggregation of an amyloid polypeptide is a concentration and time dependent event. The amyloid polypeptide is dissolved in an appropriate buffer, preferably in a buffer solution having an ionic strength comparable to physiological conditions, such as phosphate-buffered saline (PBS), TRIS™ buffer, HEPES™ buffer, or NEUROBASAL™ medium. Aggregated amyloid polypeptide is detected by routine methods, e.g., as described below.

An amyloid-binding dye can be contacted with the amyloid polypeptide prior to aggregation or after aggregation to evaluate aggregation form. The amyloid-specific spectroscopic probe can be provided at about the same concentration (molar concentration) as the amyloid polypeptide, or about an order of magnitude greater or lower, provided that (a) the spectroscopic signal from the dye can be detected on available spectrometers and (b) that the signal from the dye complexed with the polypeptide aggregate is detectable above the signal from uncomplexed dye. These factors are readily determined experimentally.

Aggregation of Aβ. After a concentration-dependent lag period during in vitro incubations, soluble preparations of synthetic AB slowly form fibrillar aggregates that resemble natural amyloid and are measurable by sedimentation or Thioflavin-T-based fluorescence. The rate of aggregation of soluble Aβ in these in vitro assays is enhanced by addition of small amounts of pre-aggregated β-amyloid "seed" material.

In a specific embodiment, Aβ(1–40) dissolved in 100% hexafluoroisopropanol at 200 or 400 μM is dried under a nitrogen stream. Hexafluoroisopropanol initially converts conformation of the peptide to a random coil state. The peptide film is dissolved in PBS buffer, pH 7.4, to a final concentration of 50 μM with brief sonication, of about five to forty seconds, and brief vortexing, for five seconds or less. This solution is then aged to permit aggregation.

Alternatively, synthetic, HPLC-purified peptides representing the first 28 (Aβ 1–28) and the first 40 amino acids (Aβ 1–40) of the 42 amino acid Aβ may be obtained from Bachem (Torrance, Calif.). Aggregation of soluble Aβ 1–28 or Aβ 1–40 at different concentrations can be initiated by addition of 0.1 M sodium acetate (NaOAc) at pH between 4.7 and 7.5. Quantitative aggregate formation with submillimolar Aβ concentrations may be detected using the procedure of LeVine (Protein Science, 1992, 2:404–410). Briefly, fluorescence of aggregates added to 10 μM Thioflavin-T (Aldrich)/50 mM potassium phosphate buffer, pH 6.0, are measured upon excitation at 450±5 nm and detection of emission at 482±10 nm on a Perkin Elmer LS-50B spectrofluorimeter.

Aggregation of Aβ at lower (physiological) concentrations may be quantitated by the method of Burdick et al. (J. Biol. Chem., 1992, 267:546–554). Synthetic preparations of Aβ may be diluted to 5 nM final concentration, preferably in the presence of "seeds." After various incubation periods at 37° C., aggregation reactions may be evaluated.

Aggregation of amylin. After a concentration-dependent lag period during in vitro incubations, soluble preparations of synthetic amylin slowly form fibrillar aggregates that resemble natural amyloid (Lorenzo et al., Nature, 1994, 368:756–760) and are measurable by electron microscopy or by Congo Red birefringence under polarized light (Fraser et al., Biophys. J., 1991, 90:1194–1201). Aggregation of soluble amylin in these in vitro assays is expected to be enhanced by addition of small amounts of pre-aggregated amylin "seed" material.

In a specific embodiment, synthetic, HPLC-purified peptides representing the 37 amino acid human or rat islet amyloid polypeptide or amylin may be obtained using standard peptide synthetic methods or from a commercial source, such as Bachem (Torrance, Calif.) or Peninsula Laboratories. Quantitative aggregate formation with sub-millimolar amylin concentrations may be detected using the procedure of LeVine (Protein Science, 1992, 2:404–410). Briefly, fluorescence of aggregates added to 10 $\mu$M Thioflavin-T/50 mM potassium phosphate buffer, pH 6.0, can be measured upon excitation at 450±5 nm, and detection of emission at 482±10 nm on a Perkin Elmer LS-50B spectrofluorimeter. Alternatively, Congo red birefringence under polarized light can be used to detect aggregation (Fraser et al., supra). Small amounts of pre-formed aggregates or "nucleation seeds" may be added to the soluble amylin and aggregation initiated, e.g., with 0.1 M sodium acetate. Soluble amylin (250 $\mu$M) and 0.2 M sodium phosphate buffer, pH 7.5, may be incubated at 37° C. to generate pre-formed aggregates referred to as "amylin seed." After incubation, protein concentrations of seed preparations are measured and adjusted with buffer to 150 $\mu$M final concentration.

Aggregation of amylin at lower (physiological) concentrations may be quantitated by the method of Burdick et al. (J. Biol. Chem. 267:546–554, 1992). Synthetic preparations of amylin is diluted to 5 nM final concentration, preferably in the presence of various "seeds." After various incubation periods at 37° C., aggregation reactions can be evaluated.

Evaluation of Aggregation Form

Once a complex of the amyloid-specific spectroscopic probe with amyloid is formed, it can be evaluated spectrophotometrically. The spectroscopic properties of either the polypeptide or the dye can be analyzed, although for the polypeptide, the most relevant information is found with far-UV CD spectroscopy.

Far-UV CD Spectroscopy

The far-UV CD spectra of free polypeptide and of complexes of the amyloid-specific spectroscopic probe with aggregated polypeptide, e.g., from about 200 nm to about 260 nm, provide information about the polypeptide conformation. Indeed, this spectrum measures dichroic absorption of the polypeptide. However, while previous experimental data have demonstrated that A$\beta$ adopts a $\beta$-sheet secondary conformation when aggregated, for the first time differences in aggregate structure between different aggregated forms have been observed and can be evaluated.

The following table provides some information about conformation of aggregated A$\beta$ complexed with Congo red, a typical sulphonated diazo dye, from far-UV CD spectra:

TABLE 1

Far-UV CD Conformation Information for A$\beta$

| Spectral Property | Conformation Characteristic |
| --- | --- |
| negative extremum at 200 nm | random coil conformation |
| red shifted negative extremum at 218 nm | typical $\beta$-sheet; co-aggregation with Congo red |
| negative extremum at 225 nm | twisted $\beta$-sheet |
| increased contribution from random coil conformation | co-aggregation with Congo red |

Near-UV CD Spectroscopy

The near-UV CD spectra, e.g., from about 300 nm to about 700 nm, measures the dye absorbence and can therefore be used to evaluate different structures of a complex of the dye and amyloid. Polypeptide alone, and Congo red, do not produce an appreciable CD signal in the near-UV region. Differences in CD spectra of complexes of the dye and polypeptide aggregates are evident in the intensity and wavelength of maximum signal.

Figure 2:
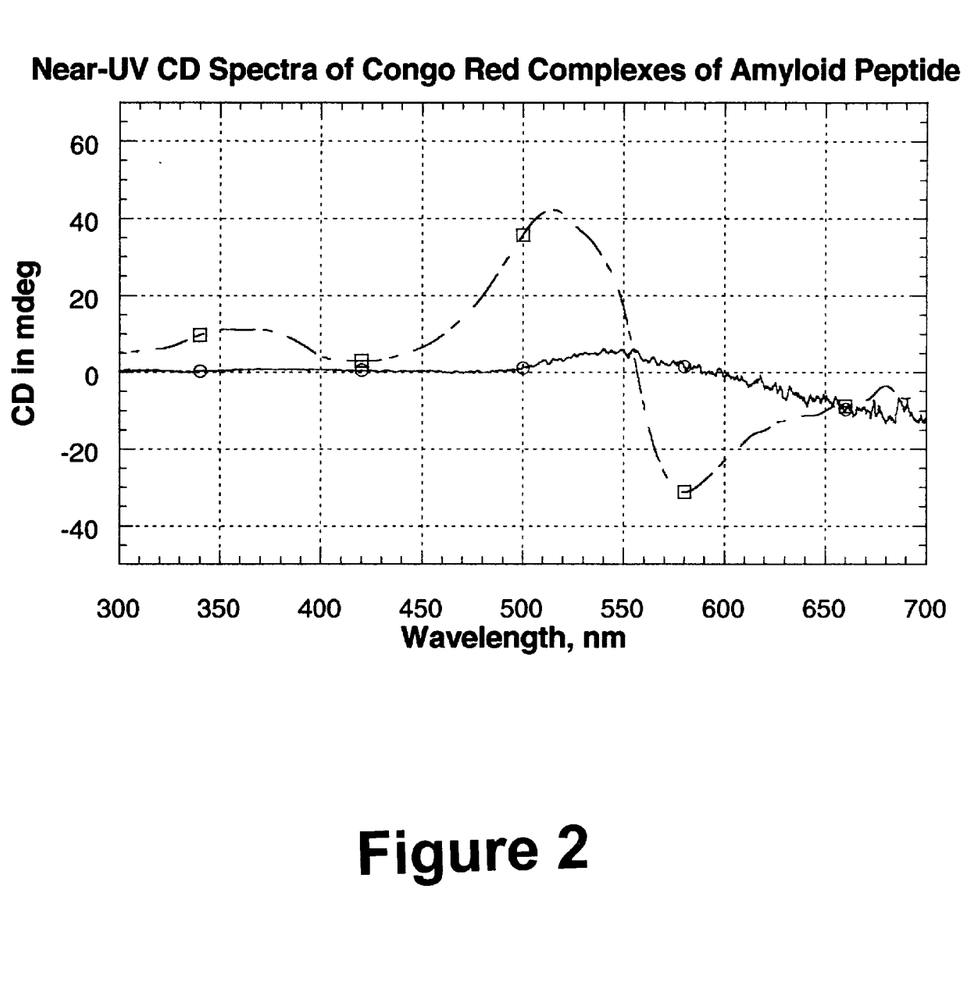
FIG. 2. Near-UV CD spectra of Congo red complexes with preformed aggregates (open square) and co-aggregates of amyloid peptide (open circle).

The following table, as well as FIG. 2, illustrates some of the conformational differences of aggregated A$\beta$ complexed with Congo red, a typical sulphonated diazo dye, from near-UV CD spectra:

TABLE 2

Near-UV CD Conformation Information for A$\beta$

| Spectral Property | Conformational Characteristics |
| --- | --- |
| negative absorption at 580 nm | Congo red complexed with pre-formed aggregate |
| positive absorption maxima at 516 and 370 nm | Congo red complexed with pre-formed aggregate |
| positive band centered at 550 nm | Congo red co-aggregated with A$\beta$ |
| exciton coupled CD spectra | complexation of Congo red with an ordered $\beta$-sheet |
| CD absorption | co-aggregates weaker than complexes of pre-formed aggregates with Congo red. |

UV Spectroscopy

UV spectral analysis can differentiate the absorption spectra of complexes of the dye with different aggregation forms. For example, Congo red has different UV absorption and difference spectral properties depending on whether it is complexed with pre-aggregates or co-aggregates of polypeptide. It is preferable to subtract the aggregated amyloid polypeptide spectra from the complexation spectra to specifically probe the absorption properties of the dye.

Alternatively, differential dye UV absorbance spectra can be obtained by subtracting normal absorbance of the dye from the absorbance of the dye complexed with aggregated amyloid polypeptide.

UV absorption spectra can be obtained from about 200 nm to about 700 nm; preferably from about 250 nm to about 700 nm. The difference in spectra (see, FIG. 4) of complexes of Congo red with amyloid peptide acquired against free Congo red show that complexes are hyperchromic, with increased absorbency around 550 nm, relative to the absorption of free form. Absorption spectra of both complexes, Congo red bound to preformed aggregates and co-aggregates, show negative absorption around 480 nm in the difference spectrum. The origin of the spectral differences is due to the conversion of free Congo red to its bound form, therefore producing a bathochromic shift in its absorption spectrum. Inspection of spectra in FIGS. 3 and 4 also suggest that the absorption enhancement between 500 nm and 550 nm is greater in the case of complexes of Congo red with preformed aggregates than in the co-aggregates. Complexation of Congo red with amyloid peptide results in a decrease in light absorption around 480 nm which is due to the free form of the compound, and a concurrent increase in light absorption between the spectral range of 500 to 550 nm, which is due to complexation.

Fluorescence Spectroscopy

Fluorescence emission or excitation spectra of the dye, e.g., Congo red, can be used to probe the aggregation form of amyloid. Fluorescence spectra of complexes of Congo red with amyloid polypeptide are shifted to slightly longer wavelengths (red shift) compared to the emission spectra of the free form of Congo red. Emission spectra of Congo red were recorded using an excitation wavelength of 500 nm. Emission maximum of the complexes of Congo red are centered at about 605 nm. Emission spectra of free Congo red and Congo red in the presence of fresh polypeptide (monomeric peptide) is centered around 620 nm. The excitation spectra of the free and bound forms of Congo red are also significantly different. The excitation maximum of the bound form of Congo red in both the coaggregates and in the complexes of preformed aggregates is centered around 525 nm. These spectra are therefore significantly red shifted relative to the free form of Congo red. The differences in the fluorescence spectra are due to changes in the microenvironment of Congo red upon binding to amyloid polypeptide.

In addition to the intensity-based measurements, other fluorescence techniques, such as (i) fluorescence anisotropy methods, and (ii) time resolved fluorescence emission measurements to identify and resolve decay times of Congo red in the presence of complexes of co-aggregates and preformed aggregates would be useful in differentiating amyloid structures.

Fluorescence Anisotropy Method

Polarization or anisotropy of fluorophores occur due to angular displacement of the fluorophore between absorption and emission of light. The angular displacement is dependent upon the rate and extent of rotational diffusion during the lifetime of the excited state of the fluorphore (Lakowicz, J. R., Principles of Fluorescence Spectroscopy, Plenum Press, New York, 1983). The diffusive motions are dependent on several parameters, the most important one for the current application being change in molecular size and shape of the amyloid protein. Fluorescence anisotropy methods may be used to determine the increase in molecular size of the amyloid protein due to protein-protein interactions upon aggregation in the absence and presence of test compounds. More specifically, the polarization measurements are based on the principle that small molecules are "isotropic"; that is, they freely rotate in solution. When they are bound or attached to a macromolecule, the rotation and tumbling movements are slower, thereby rendering the emission anisotropic. When autofluorescent small molecules are used as probes, the emission of the molecule becomes "polarized" (Lee, Y. C., J. Biochem., 1997, 121(5):818–825) upon binding to a macromolecule. The changes in fluorescent properties can be used in two ways. In the first, changes in fluorescence anisotropy of small molecules such as Congo red may be used to determine if the molecular sizes of the complexes of the protein are different. In the second method, amyloid polypeptide can be directly labeled with fluorophore to determine the molecular sizes of the protein in the two different instances.

In the first case, in a typical experiment, fluorescence polarization of free Congo red would be measured in the absence of amyloid protein. The increase in anisotropy value of the bound form of Congo red in the complexes of the co-aggregates of test compounds relative to its free form, can then be used to estimate the differences in size and shape of amyloid protein, as a means to determine the effects of test compounds on polypeptide aggregation.

In the second instance, a fluorophore-labeled amyloid peptide can be used to differentiate aggregates formed in the presence of the Congo red or test compound. Fluorophores such as ruthenium bipyridyl complexes, fluorescein, and rhodamine are useful probes in anisotropy assays. The ruthenium ligand complexes are especially suited for differentiating the molecular size of large molecular weight proteins. Ruthenium bipyridyl complexes have long decay times, on the order of 400 ns, compared to other fluorophores such as fluorescein or rhodamine groups whose fluorescence lifetimes are normally on the order of 10 nanoseconds. The longer decay times of ruthenium complexes are suitable for probing the molecular weight of larger protein molecules that tumble at a much slower time scale in solution. Fluorophores such as fluorescein, on the other hand, are useful in differentiating smaller oligomers of Aβ peptide within a molecular weight and size corresponding to 50,000 daltons.

In a typical experiment, the test compound or Congo red are aggregated in the presence of amyloid protein. Aβ peptide can be conjugated to fluorophores such as fluorescein, rhodamine, or ruthenium using standard coupling chemistry of succinimidyl esters and isothiocyanate groups to obtain labeled peptide (Szmacinski et al., Biophys. Chem., 1996, 62:109–120). In an initial experiment, the steady state anisotropy of the free fluorophore is determined. The anisotropy value of the labeled peptide would be small due to rapid tumbling motions or the molecules. Aging of the fluorescent peptide in the presence of amyloid protein would increase the anisotropy value of the fluorophore, due to an increase in molecular size and change in shape of the amyloid protein. Since the labeled peptide is mainly used as a fluorescence probe, its concentration would typically be about 10-fold to about 1000-fold lower than the concentration of amyloid protein.

In a second experiment, the fluorescence anisotropy value of the labeled peptide contacted with amyloid protein and test compound during aging is determined. The increase in anisotropy is due to an increase in the molecular size of the protein. Alternatively, the increase in anisotropy values can be used to determine the rate of formation of higher molecular weight aggregates to identify the effects of test compounds.

Time Resolved Fluorescence

Fluorescence decay kinetics of fluorophores, such as Congo red or the fluorescent labeled peptide (described in the fluorescence anisotropy method), can be used to identify and differentiate complexes of test compound with amyloid proteins. This method is based on the premise that the fluorescence lifetime is altered upon binding to protein due to changes in the radiative and non-radiative decay rates of the bound and free forms of the inhibitor. The fluorescence lifetime of Congo red can be measured using a frequency-domain or a time-domain instrument. For example, a parameter, mean lifetime, of Congo red or the fluorescent labeled peptides can be estimated. The mean lifetime is a function of lifetimes and concentrations of the bound and free forms of the fluorophore. Alternatively, the lifetime-based approach can also be applied to live neuronal cultures. A distribution of lifetimes may be estimated for free and complexed forms of Congo red using fluorescence imaging of the cell. This method of two dimensional imaging (FLIM or Fluorescence Lifetime Imaging) provides a distribution of Congo red on a cell-by-cell basis as they pass through a laser beam using a phase flow cytometer. The secreted and extracellular forms of amyloid proteins can be identified using the FLIM method. The FLIM approach is very useful in detecting amyloid protein secreted into the medium in cell cultures or in tissue samples.

Infrared and NMR Spectroscopy

Infrared absorption spectra of amyloid protein is a useful tool to determine the structure of amyloid protein in the aggregates when complexed with test compounds or Congo red. The frequency of the amide I band, representing the carbonyl stretching vibration of the peptide bond, is sensitive to conformation of peptide backbone and, therefore, the secondary structure of polypeptide. The amide I band of the β-sheet structures absorb at 1620 to 1640 cm$^{-1}$ and weakly at a higher frequency of 1680 to 1695 cm$^{-1}$. Changes in the conformation of amyloid polypeptide when the poypeptide is aggregated in the absence and presence of test compounds or sulphonated dyes can be interpreted on the basis of differences in the amide I absorption band.

NMR is similarly useful in obtaining structural information on the protein when aggregated in the absence and presence of test compounds or Congo red. The structure of amyloid polypeptide may be elucidated using chemical shifts, preferably of protons or other nuclei such as $^{13}C$ or $^{15}N$. The chemical shift of protons are more commonly used for structure assignments. It has been well documented in the literature that β-sheet regions show downfield shifts for the $^{\alpha}H$ resonance. Helical regions on the other hand show upfield shifts. On the basis of data set containing 5000 amide protons and $^{\alpha}H$ shifts, the mean $^{\alpha}H$ positions in helices and sheets differ by nearly 0.8 ppm with very little overlap between the two distributions (Methods in Enzymology, vol. 239, Part C. pp. 363–392 (1994)). This general trend holds true for the amide protons as well and therefore the β-sheet form can be identified. Amide protons at the N-terminus of helices tend to be shifted downfield compared to those at the C-terminus. Such chemical shifts in the proton resonances can be therefore used to assign structural differences of polypeptide in monomers and aggregated states in the absence and presence of test compounds.

Analytical Ultracentrifugation

In conjunction with the spectroscopic methods, analytical ultracentrifugation methods are useful in determining the solution molecular weight and to assess the degree of molecular homogeneity of amyloid polypeptide. The sedimentation methods can be used to rapidly determine if aggregates of amyloid polypeptide exist in solution and if the aggregate is reversible or irreversible in nature. There are essentially two sedimentation methods: sedimentation velocity and sedimentation equilibrium. The first method provides rapid means for estimating size, shape, and molecular weight of the aggregated polypeptide. The latter method is useful in determining the buoyant molecular weight of polypeptide. The difference in the average molecular weight of polypeptide aggregated in the absence and presence of test compounds may be determined using sedimentation velocity and equilibrium methods. Application of these methods helps in differentiating the size and nature of aggregates such as those formed in the presence of Congo red or other test compounds, and also to evaluate efficacy of test compounds in arresting aggregation of polypeptide at the nucleation step or further along during elongation step. This information complements the structural information obtained by spectroscopic methods.

Assays

One or more of the foregoing spectroscopic techniques, optionally in conjunction with a non-spectroscopic technique such as ultracentrifugation, can be used to determine the effect of a test compound evaluated for its ability to inhibit or reverse amyloidosis in vitro. Indeed, by combining information from the results of more than one, and preferably all, of the spectroscopic techniques described in this application, it will be possible to determine with some detail and certainty how the test compound affects amyloid formation. These data have very important implications for screening and testing for compounds to treat diseases or disorders associated with amyloidosis, particularly Alzheimer's disease.

As used herein, the term "compound" refers to any molecule or complex of more than one molecule that affects amyloidosis. The present invention contemplates screens for synthetic small molecule agents, chemical compounds, chemical complexes, and salts thereof as well as screens for natural products, such as plant extracts or materials obtained from fermentation broths. Other molecules that can be identified using the screens of the invention include proteins and peptide fragments, peptides, nucleic acids and oligonucleotides, carbohydrates, phospholipids and other lipid derivatives, steroids and steroid derivatives, prostaglandins and related arachadonic acid derivatives, etc.

In one embodiment, the test compound is incubated with the soluble amyloid polypeptide under conditions which lead to aggregation, i.e., amyloid formation or amyloidosis. The resulting material, which may or may not be an aggregate, is then contacted with the amyloid-specific spectroscopic probe, and one or more spectra obtained. In a further embodiment, the test compound is removed from the polypeptide prior to adding the dye.

In another embodiment, the dye is present with the test compound and the soluble form of the amyloid polypeptide prior to inducing aggregation.

In yet another embodiment, a pre-formed aggregate of amyloid polypeptide is treated with a test compound to determine what effect, if any, the test compound has on the aggregate. This effect can be evaluated by contacting the aggregate with the dye after incubating it with the test compound.

In still another embodiment, the test compound itself may be an amyloid-specific spectroscopic probe or a related molecule with chromophoric, and preferably fluorophoric, properties. Thus, the test compound can be used to probe the aggregate form as well as to disrupt or inhibit the aggregate form.

The UV and fluorescence spectroscopic techniques can be readily adapted to high throughput screens, because they can be modified to rely on a single read-out for immediate structural information. However, by using all of the techniques across the entire relevant spectrum, it is possible to identify more subtle changes in the aggregated form that would aid in identifying promising compounds from a collection of candidate test compounds.

Although the assays are conducted in vitro to permit spectroscopic analysis, it is possible to use an amyloid polypeptide from any source, i.e., natural or synthetic polypeptides. For example, cerebrospinal fluid, which may contain Aβ, can be tested. In another embodiment, blood, serum, or plasma, which may contain one of the different amyloid polypeptides, can be tested. In a further embodiment, the amyloid polypeptide from one or more of these sources can be isolated and tested in a standard buffer, since body fluids, such as CSF and blood or blood products, may interfere with obtaining clear spectra.

EXAMPLES

The present invention will be better understood by reference to the following examples, which are provided by way of illustration and not by way of limitation.

Example 1
Characterization of Fibrillogenesis of Amyloid Peptide

There is continuing interest to determine the effect of small molecule inhibitors on the self assembly of amyloidogenic peptides and the coincident effect on cytotoxicity. Towards this goal, quantitative fluorescence and CD methods were implemented to determine the extent of fibrillization of peptide, in the presence and absence of Congo red. This work shows (i) the simultaneous assessment of the formation of β-pleated sheet conformation using changes in the fluorescence of Thioflavin T and CD spectroscopy; (ii) the effect of medium on the rate of aggregation of peptide; (iii) toxicity of aggregated peptide to hippocampal cell cultures using release of LDIH as an indicator; and (iv) the interaction of Congo red with peptide in the presence of thioflavin.

Methods

Fluorescence Spectroscopy. Thioflavin binds amyloid fibrils to induce a characteristic hyperchromic fluorescence shift in the spectrum (LeVine, J. Exp. Clin. Invest., 2:1–6, 1995). The induced fluorescence due to thioflavin is specific for amyloid β-pleated fibrils, but not for other β-sheet structures or for the soluble oligomeric forms of the peptide. Free thioflavin is a weak fluorophore with an excitation maximum at 330 nm. Upon binding to the amyloid fibrils, the fluorescence of thioflavin is enhanced with a red shift in the excitation spectrum by 100 nm, relative to the free form. We have used the increase in fluorescence intensity at excitation and emission wavelengths of 440 nm and 485 nm, respectively, to characterize the aggregation event.

It was determined that the induced fluorescence of thioflavin is quenched significantly in the presence of Congo red. In these experiments, thioflavin was complexed with aggregated peptide prior to titration with increasing amounts of Congo red. The resulting decrease in fluorescence intensity is due to energy transfer of the fluorescence emission of thioflavin to Congo red. Therefore, assays that rely on thioflavin alone are likely to generate false positives in primary assays, while spectroscopic assays described in this invention would identify the more promising inhibitors of amyloidogenesis.

Circular Dichroism Spectroscopy. Conformational change of the peptide from the random coil to the β-sheet form, during aging, was monitored using changes to the molar ellipticity of the peptide at 200, 218, or 225 nm. This assay was also used to determine if the changes in the CD spectra occurred concurrently with the changes in the fluorescence spectra of thioflavin. The CD spectrum of the peptide was scanned at various time points to correlate the formation of thioflavin-binding macromolecular assemblies with the appearance of β-sheet conformation.

Spectroscopic Assays. To determine the extent of aggregation, aliquots of the peptide were removed at various time intervals (up to nine hours), and diluted into PBS buffer-containing 10 $\mu$M thioflavin. The final concentrations of peptide and thioflavin in the fluorescence assay were 10 $\mu$M. The fluorescence intensities of the peptide-thioflavin complex were measured at excitation and emission wavelengths of 435 and 485 nm, respectively, after the reaction had equilibrated for five minutes. Fluorescence spectral scans were made using 435 nm excitation and 485 nm emission wavelengths using a SPEX™ fluorolog-2 spectrofluorometer (Instruments S.A.®, Jobin Yvon-Spex, Edison, N.J.). For the Congo red experiments, peptide-thioflavin complex was titrated with increasing concentrations of Congo red from 0.1 to 3.5 micromolar concentrations. The fluorescence intensity changes were measured at the above-mentioned spectral wavelengths. When fluorescence intensities were measured in a plate reader, the peptide was diluted into PBS buffer-containing 10 $\mu$M thioflavin, to a final volume of 100 $\mu$L.

CD spectra were recorded on a JASCO™ spectropolarimeter model J715 (Jasco, Easton, Md.) at room temperature in a 0.1 cm pathlength cell. Typically, the peptide samples were aliquoted at various time intervals for fluorescence and the CD spectra were scanned using the remaining solution. The CD spectra of the peptide were recorded in the far-UV between 190–260 nm. The spectral results are expressed as deg.cm$^3$.dmol$^{-1}$.

Neurotoxicity Assay. Peptide was aggregated according to the end points determined in the CD and fluorescence assay and applied to primary neuronal cell cultures to assess cytotoxicity of the aggregated peptide. The release of LDH was used to monitor cell viability in the presence of Aβ and Congo red.

Aβ(1–40) toxicity was assessed using eight day-in-vitro (DIV) rat fetal (E18) hippocampal cultures. The cells were cultured in 48-well dishes previously coated with 500 $\mu$l/well of 0.1 mg/ml of poly-L-lysine (100 $\mu$l/well) and, subsequently, with 100 $\mu$l/well of 5 $\mu$g/ml of mouse laminin. The cells were seeded at a density of 92,300 cells/well in a total volume of 500 $\mu$l of NEUROBASAL™ medium containing 1XB27 supplement, 5% heat inactivated and qualified fetal bovine serum, 0.5 mM glutamine, 50 $\mu$/ml penicillin, and 0.05 mg/ml streptomycin, and were initially placed in humidified 5% $CO_2$ in air. After twenty-four hours, the medium was replaced with fresh medium lacking the penicillin, streptomycin, and fetal bovine serum and the cultures were thereafter maintained in air containing 5% $CO_2$ and 9% $O_2$. Fresh medium was substituted into each well on day five. On the seventh day in vitro, the medium was replaced with antioxidant free B27 supplemented medium lacking the penicillin, streptomycin, and fetal bovine serum. The toxicity test was initiated on the eighth day in vitro by substituting into each well 500 $\mu$l of the medium used on day seven (as the control treatment) or an experimental solution prepared with the final (control) medium. Each experimental solution was tested on cultures contained in five wells. Toxicity was assessed on the eleventh day in vitro using the lactic acid dehydrogenase (LDH; Sigma 340-UV) assay. Aggregated peptide was diluted five-fold to a final concentration of 10 uM, for the toxicity assays. Complexes of Congo red with preformed aggregates and those formed in co-aggregates were tested in the cellular assays along with aggregated peptide in vehicle controls.

Preparation of Amyloid Peptide. Aβ(1–40) was purchased from Anaspec (San Jose, Calif.) and its chemical purity was verified using reverse phase HPLC, ESI-MS and protein sequencing methods. The lyophilized peptide was dissolved in hexafluoroisopropanol (HFIP) solvent to aid in disaggregation of peptide. Peptide in HFIP solvent, was stored at −80° C. Prior to use, peptide solution was thawed and the solvent was evaporated under a stream of nitrogen. The peptide was dissolved in buffer to obtain a concentration of 50 $\mu$M, sonicated approximately twenty to forty seconds, and then vortexed briefly, approximately five seconds or less, to aid dissohltion of peptide. To determine the effects of media on the rates of aggregation, peptide was dissolved in one of the following buffers: PBS, 50 mM HEPES™ or in NEUROBASAL™ medium. Peptide solutions were dispensed into microtiter plates at a final concentration of 45 $\mu$M in 100 $\mu$L. Aggregation was initiated by shaking plates continuously in a rotary shaker.

Results

The appearance of thioflavin-binding structures is concurrent with the formation of the β-sheet conformation of the peptide. Higher pH and ionic strength promote aggregation of peptide (Table 3).

TABLE 3

Effect of buffer and medium on the rate of aggregation of Aβ (1–40)

| Aggregation Time, hr | Percent Aggregation in NEUROBASAL ™ Medium | Percent Aggregation in PBS* | Percent Aggregation in HEPES ™ |
|---|---|---|---|
| 0 | 0 | 0 | 0 |
| 1 | 0 | 0 | 0 |
| 2 | 76 | 51 | 0 |
| 4 | 100 | 100 | ++ |

Each value is an average of three determinations.
++ indicates aggregates were formed but not quantitated because end point was not reached. Percent aggregation was calculated relative to fluorescence of thioflavin/Aβ at 0 and 4 hr. The peptide was agitated in a rotary shaker at a speed of 500 rpm in this experiment.
*The relative rates of aggregation are very sensitive to the speed of agitation.

Amyloid peptide changes from a random coil form to an altered β-sheet conformation upon aging in PBS for nine hours. The altered conformation has a CD absorption band with a broad negative extremum at 225 nm. The red shifted-CD spectrum is likely due to the formation of twisted β-sheet structures.

The fluorescence emission of thioflavin is quenched significantly by nanomolar concentrations of Congo red. The extent of quenching leveled off at micromolar concentrations of Congo red, therefore indicating that an initial site on the peptide is saturated. The fluorescence of peptide-bound thioflavin was quenched by greater than one order of magnitude by Congo red, while the quenching effect was only 50% in the case of free thioflavin. The observation that the fluorescence intensity is quenched by Congo red is consistent with co-localization of Congo red and thioflavin on aggregated peptide.

Congo red is neuroprotective to cell cultures exposed to βP. Congo red complexed with preformed aggregates and in co-aggregates attenuates the toxicity of Aβ. Aggregated peptide (samples aged for four hours) is toxic to neuronal cultures, while fresh peptide is non-toxic, in 72 hour toxicity assays.

Discussion

This Example has shown that conversion of random coil to β-sheet conformation occurs concurrently with the formation of thioflavin-binding oligomeric structures of the peptide. Congo red and thioflavin bind non-competitively with aggregated peptide.

Example 2
Spectroscopic Evaluation of Congo Red-Amyloid Complexes

Amyloid peptide (Aβ) was aged in the absence and presence of Congo red as described below: Aβ (1–40) was dissolved in 100% hexafluoroisopropanol to produce a final concentration of 200 or 400 μM. To aid dissolution of peptide, the solution was sonicated briefly, for about five seconds. An appropriate volume of the peptide solution was transferred to an amber vial and the solvent was evaporated under a stream of nitrogen. The peptide film was dissolved in PBS buffer, pH7.4, to a final concentration of 50 μM. The peptide solution was sonicated for 20 seconds and then vortexed for about five seconds. To prepare coaggregates of peptide with Congo red, the dye was added to peptide at a final concentration of 10 μg/mL, 20 μg/mL or 30 μg/mL. The stock solutions of the peptide (peptide in vehicle control and peptide plus Congo red), were aliquoted into microtiter plates at a final volume of 100 μL per well. Aggregation was initiated by shaking plates at 500 rpm.

To determine the extent of fibrillization, an aliquot of the peptide samples was withdrawn and diluted five-fold into PBS buffer containing 10 μM of the fluorophore, thioflavin T. The final concentration of peptide in the samples was 10 μM. The fluorescence emission spectra of free thioflavin and peptide-Thioflavin complexes were scanned using a fluorometer, in this instance a SPEX™ fluorometer. The increase in fluorescence of thioflavin T at an excitation wavelength of 450 nm (emission monochromator at 485 nm) indicated the formation of fibrillar peptide. Alternatively, a plate fluorometer was also used in some experiments to measure the extent of fibrillization. In these experiments, fluorescence of thioflavin T was measured in a TECAN™ Plate fluorometer (Tecan U.S. Inc., Research Triangle Park, N.C.) using an excitation filter of 440 nm and an emission filter of 490 nm.

CD spectroscopy was used to determine the time course of aggregation in the presence of Congo red and the conversion of the peptide from a random coil form in the freshly prepared state to a β-sheet form in the aged state. Aging of peptide for nine hours produced a red shifted β-sheet spectrum, perhaps due to the formation of twisted β-sheet structures.

To prepare complexes of Congo red with preformed fibrils, aged peptide was combined with Congo red at final concentrations of 10 μg/mL, 20 μg/mL and 30 μg/mL.

CD Analysis

Figure 1:
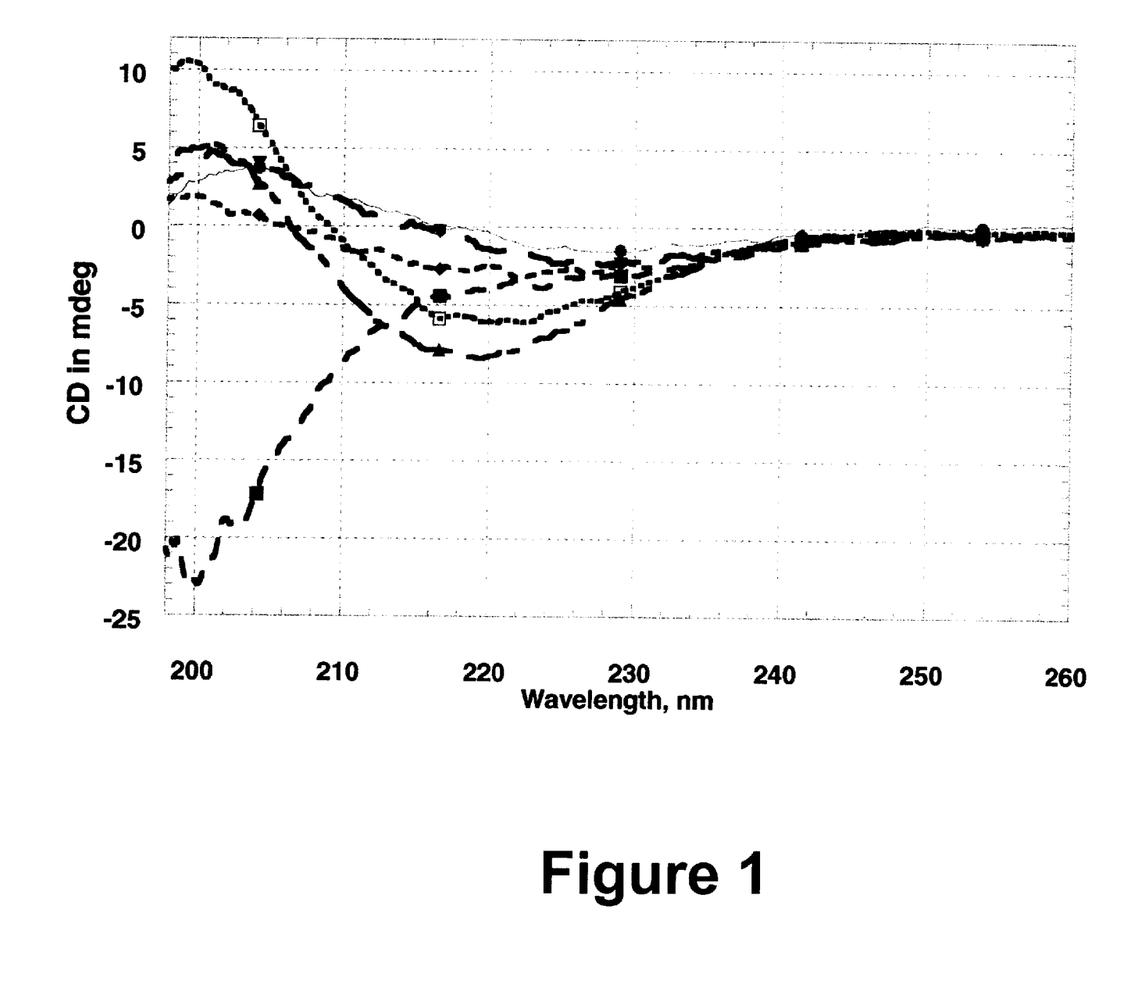
FIG. 1 (color). Effect of Congo red on the conformation of Aβ(1–40). Far-UV CD spectra of complexes of Congo red with aged and fresh peptide were compared to far-UV CD spectra of co-aggregates to determine the differences in the conformation of the peptide aggregate. Green/diamond: co-aggregates at 14.3 μM Congo red; purple/open square: co-aggregates at 21 μM Congo red; red/triangle: co-aggregates at 47 μM Congo red; blue/inverted triangle: aged amyloid peptide; orange/square: fresh peptide with 21 μM Congo red; thin orange/circle: aged peptide with 21 μM Congo red.

Far-UV CD spectra of the complexes of Congo red with pre-aggregated peptide and peptide coaggregates, were scanned between 200 nm to 260 nm (FIG. 1). The negative extremum at 200 nm indicates a random coil conformation of the fresh peptide.

Aging induced a conformational change to a β-sheet form. The CD spectrum of the peptide aged in the absence of Congo red consisted of a negative extremum at 225 nm and a positive extremum at 205 nm. This red-shifted negative absorption at 225 nm is likely due to the formation of twisted β-sheet structures. This red-shifted CD spectrum of the preformed aggregates of the peptide was not altered by complexation with Congo red.

In contrast to the CD spectrum of preformed aggregates, the CD spectrum of the peptide aged in the presence of Congo red (coaggregates) consisted of a negative CD absorption band around 218 nm due to folding of the peptide into a typical β-sheet conformation. The CD spectrum also provided evidence for increased contributions from random coil form in the coaggregates, therefore suggesting that the aggregation rate was slowed down in the presence of Congo red. The differences in the CD spectra of the two forms of peptide were due to an increase in random coil form in the coaggregates and also to the formation of altered aggregation states of the peptide.

The near-UV CD spectra of the peptide samples were scanned between 700–300 nm. This region is useful in differentiating the Congo red complexes. Peptide alone in buffer and free Congo red did not produce an appreciable CD signal in the near-UV region. The differences in the CD spectra of the coaggregates and the preformed aggregates were evident in the intensity and the wavelength of maximum absorption; the CD spectrum of the coaggregates was weaker than the CD spectrum of the pre-formed aggregates (FIG. 2; see, Table 2). The CD spectrum of pre-aggregated complexes of peptide with Congo red consisted of negative absorption at 580 nm and a positive absorption band at 516 nm. The intensity of the CD bands was proportional to the concentration of the complexes. The CD spectrum of coaggregates consisted of a positive band centered at 545 nm. The differences in the spectra of the complexes are due to the formation of different complexation states of Congo red. The exciton coupled CD spectra are indicative of complexation of Congo red with an ordered β-sheet conformation of peptide.

UV Spectral Analysis

UV spectral analysis was used to differentiate the absorption spectra of the two complexes of pre-aggregated peptide and coaggregates with Congo red.

Figure 3:
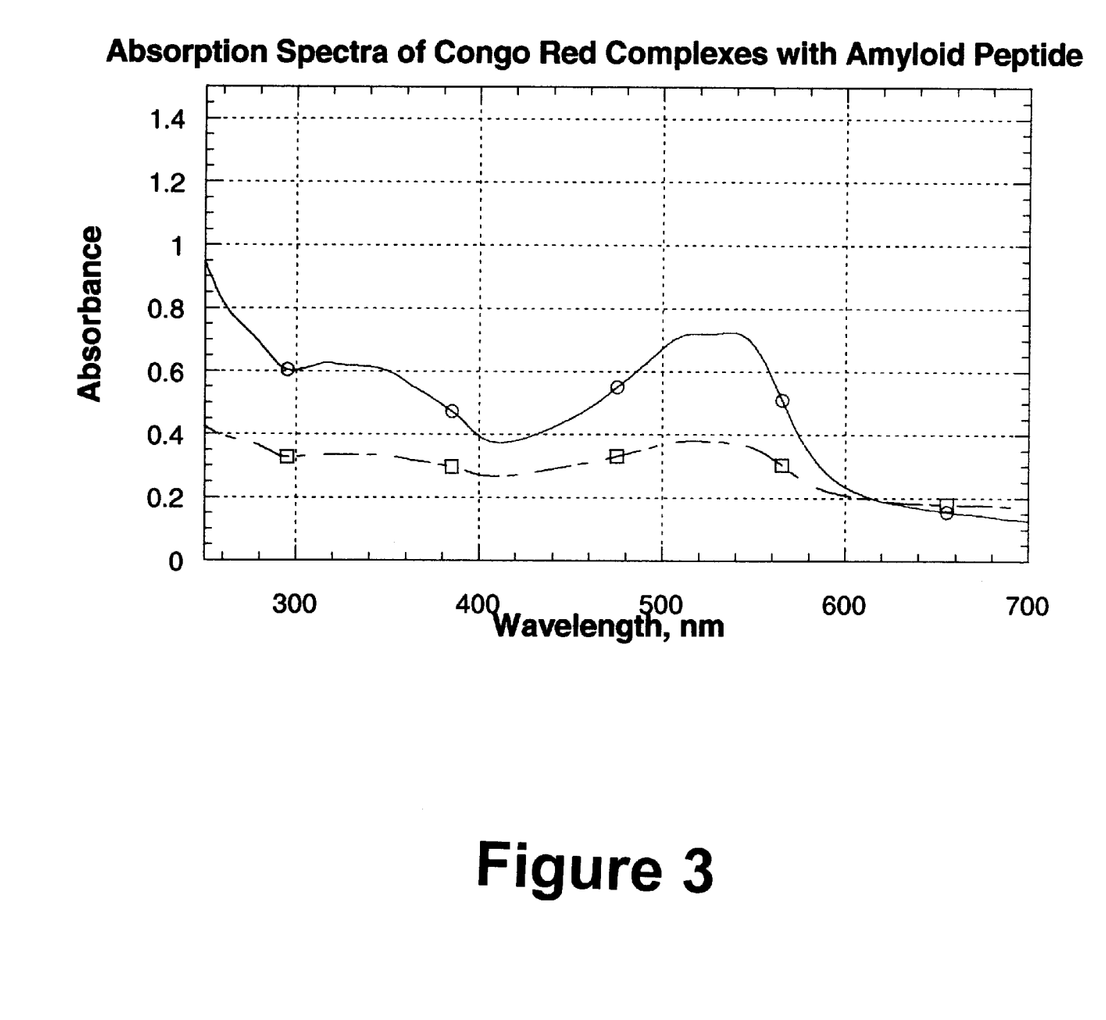
FIG. 3. Absorption UV spectra of complexes of Congo red with preformed aggregates (open circle) and co-aggregates (open square). Absorption spectra were measured against aged peptide.

FIG. 3 shows the difference in spectra of complexes of Congo red with polypeptide measured against aged peptide, wherein the complexes are in the first instance coaggregates of amyloid peptide with Congo red and, in the second instance, Congo red complexed with a preformed polypeptide aggregate. Since the total concentration of Congo red is the same in both complexes, the differences in absorption intensities would suggest that the complex with a preformed aggregate is hyperchromic relative to the coaggregate.

Figure 4:
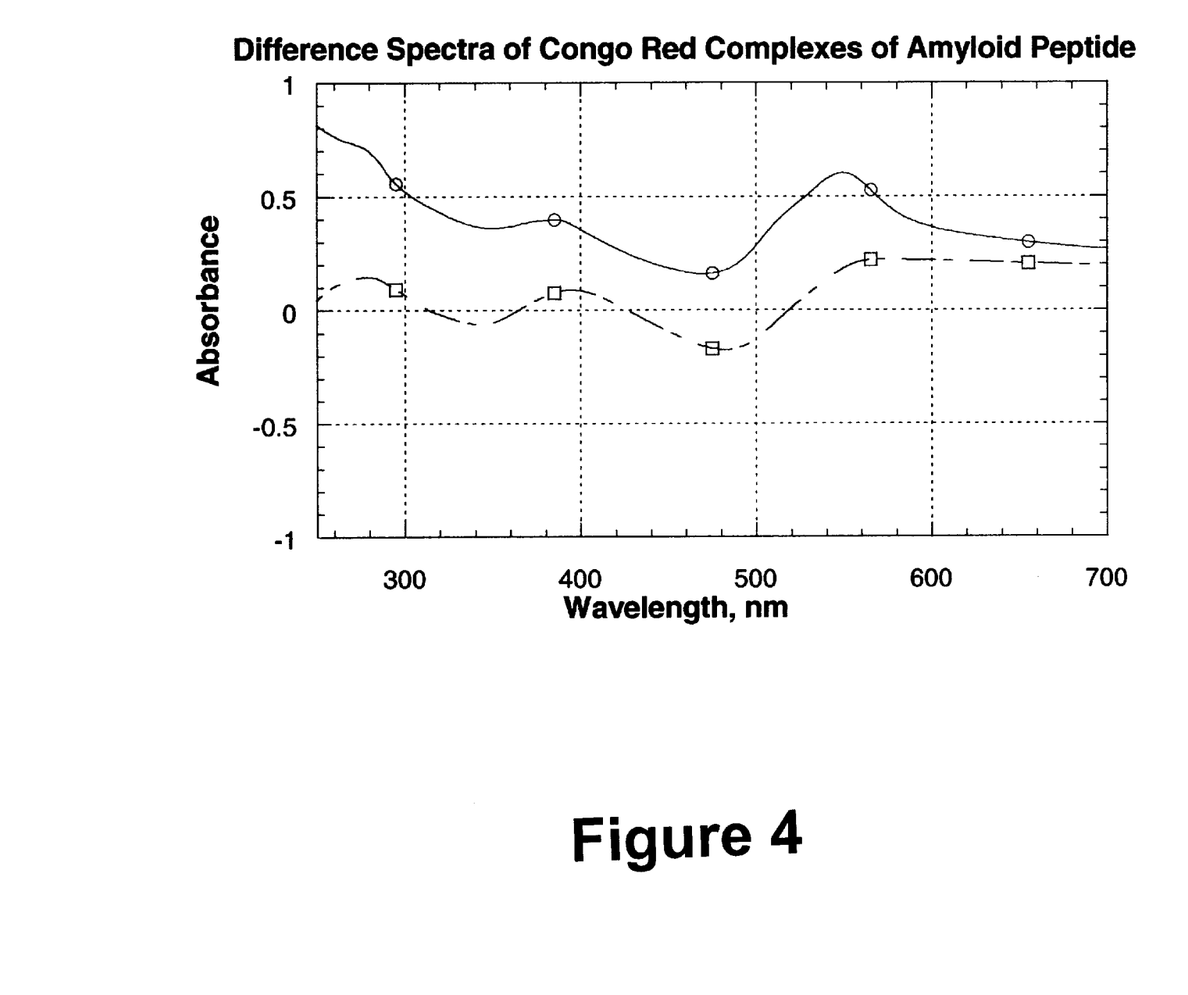
FIG. 4. Difference spectra of complexes of Congo red with preformed aggregates (open circle) and co-aggregates (open square) of βAP 1–40. The absorption spectra were measured against Congo red.

FIG. 4 shows the difference in spectra of the complexes of Congo red, co-aggregate, and preformed aggregate measured against an equivalent concentration of free Congo red is centered around 480 nm, while the absorption maxima of the complexed forms are shifted to slightly higher wavelengths. The negative absorption peak in FIG. 4 centered around 480 nm is therefore due to depletion of free Congo red because of binding to amyloid polypeptide. Similarly, a positive absorption peak centered around 530 nm, especially in the case of Congo red complex with preformed aggregate, is due to a change in the absorption property of Congo red upon complexation. This complex has an absorption maximum centered at 530 nm, while the absorption maximum of the coaggregate reaches a maximum at 530 nm and retains the absorption property beyond 530 nm. The absorption spectra of the coaggregate and the preformed complexes therefore differentiate the intrinsic absorption properties of Congo red in the coaggregates and the preformed complexes from the free state. The differences in the absorption spectra are due to changes in the environment of the peptide-bound state of Congo red relative to the uncomplexed state. Such spectral changes in Congo red are likely induced by changes in the electronic state or properties of Congo red.

Fluorescence Analysis

The fluorescence emission spectra of complexes of Congo red were obtained after diluting the peptide fivefold into a buffered solution. Congo red was added to freshly diluted fibrillar peptide and the fluorescence spectrum was scanned at a final concentration of 10 μM of peptide. The concentrations of peptide and Congo red in the fluorescence assay were 10 μM and 8.6 μM respectively. The differences in the fluorescence intensities and emission wavelengths of the coaggregates and preformed aggregate-complexes, were due to the relative differences in the hydrophobicity of the binding sites in the two instances.

Discussion

The spectroscopic results described in this Example shows that amyloid inhibitors such as Congo red form distinct complexes with amyloid peptide. While these complexes attenuate the neurotoxicity of the peptide, the medical use of these substances needs to be assessed according to the disease stage. The results described have shown that Congo red binds and therefore attenuates the toxicity of the aggregated peptide.

While Congo red does not completely inhibit conversion of the random coil form of peptide to β-sheet form, the results described above have shown that Congo red stabilizes an intermediate aggregated form of amyloid peptide. Inhibitors that produce such effects need to be carefully assessed for in vitro activity in Alzheimer's disease models to determine if such substances can be administered for therapeutic or prophylactic action. The spectroscopic methods described here can be used to identify and differentiate inhibitors of amyloidogenesis and to determine the molecular mechanism of action of anti-aggregation inhibitors that would be advanced as anti-Alzheimer's agents in drug development programs, as well as other potential inhibitors of amyloidogenic fibrillogenesis associated with other diseases or disorders.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, are approximate, and are provided for description.

All patents, patent applications, publications, and other materials cited herein are hereby incorporated by reference in their entireties.

What is claimed is:

1. A method for determining an aggregation conformation of an amyloid polypeptide, which method comprises comparing:

(a) a spectroscopic property of an amyloid-specific spectroscopic probe complexed with an amyloid polypeptide having an undetermined aggregation conformation; and (b) a predetermined spectroscopic property of the amyloid-specific spectroscopic probe complexed with an amyloid polypeptide of known aggregation conformation, wherein the aggregation conformation of the amyloid polypeptide having the unknown aggregation conformation is determined by said comparison.

2. The method according to claim 1, wherein the amyloid-specific spectroscopic probe is an amyloid-binding dye.

3. The method according to claim 2, wherein the amyloid-binding dye is a sulphonated diazo dye.

4. The method according to claim 2, wherein the amyloid binding dye is Congo red.

5. The method according to claim 1, wherein the amyloid-specific spectroscopic probe is a fluorophore-labeled peptide.

6. The method according to claim 1, wherein the amyloid polypeptide is β-amyloid (Aβ) peptide.

7. The method according to claim 1, wherein the spectroscopic properties are evaluated using far-ultraviolet (UV) circular dichroism (CD) spectroscopy.

8. The method according to claim 1, wherein the spectroscopic properties are evaluated using near-ultraviolet (UV) circular dichroism (CD) spectroscopy.

9. The method according to claim 1, wherein the spectroscopic properties are evaluated using ultraviolet (UV) spectroscopy.

10. The method according to claim 1, wherein the spectroscopic properties are evaluated using fluorescence spectroscopy.

11. The method according to claim 1, wherein the known aggregation conformation comprises a fibrillar conformation.

12. The method according to claim 1, wherein the amyloid polypeptide having the undetermined aggregation conformation is co-aggregated with the amyloid-specific spectroscopic probe.

13. A method for detecting an effect of a compound on an aggregation conformation of an amyloid polypeptide, which method comprises comparing:

(a) a spectroscopic property of a complex of an amyloid-specific spectroscopic probe and an aggregated amyloid polypeptide when the amyloid polypeptide is contacted with a test compound; and (b) a spectroscopic property of a complex of an amyloid-specific spectroscopic probe and an aggregated amyloid polypeptide in the absence of the test compound, wherein a difference in the spectroscopic properties indicates that the test compound affects the aggregation conformation of the amyloid polypeptide.

14. The method according to claim 13 wherein the amyloid-specific spectroscopic probe is contacted with a preformed amyloid polypeptide aggregate.

15. The method according to claim 13, wherein the amyloid-specific spectroscopic probe is coaggregated with the amyloid polypeptide.

16. The method according to claim 13, wherein the amyloid-specific spectroscopic probe is an amyloid-binding dye.

17. The method according to claim 16, wherein the amyloid binding dye is a sulphonated diazo dye.

18. The method according to claim 16, wherein the amyloid binding dye is Congo red.

19. The method according to claim 15, wherein the amyloid-specific spectroscopic probe is a fluorophore-labeled peptide.

20. The method according to claim 10, wherein the amyloid polypeptide is β-amyloid (Aβ) peptide.

21. The method according to claim 13, wherein the spectroscopic properties are evaluated using far-ultraviolet (UV) circular dichroism (CD) spectroscopy.

22. The method according to claim 13, wherein the spectroscopic properties are evaluated using near-ultraviolet (UV) circular dischroism (CD) spectroscopy.

23. The method according to claim 13, wherein the spectroscopic properties are evaluated using ultraviolet (UV) spectroscopy.

24. The method according to claim 13, wherein the spectroscopic properties are evaluated using fluorescence spectroscopy.

25. The method according to claim 13, wherein the amyloid polypeptide is aggregated in a fibrillar form.

26. The method according to claim 2, wherein the amyloid binding dye is Chrysamine G.

27. The method according to claim 16, wherein the amyloid binding dye is Chrysamine G.

* * * * *